(12) United States Patent
Nurmi et al.

(10) Patent No.: US 8,247,171 B2
(45) Date of Patent: Aug. 21, 2012

(54) METHOD FOR DETECTION OF PRESENCE OF TARGET POLYNUCLEOTIDE IN SAMPLES

(75) Inventors: Jussi Nurmi, The Hague (NL); Anniina Syrjälä, Turku (FI); Piia Von Lode, Paattinen (FI); Virve Hagren, Ilmarinen (FI)

(73) Assignee: Abacus Diagnostica Oy, Turku (FI)

( * ) Notice: Subject to any disclaimer, the term of this patent is extended or adjusted under 35 U.S.C. 154(b) by 260 days.

(21) Appl. No.: 12/524,200

(22) PCT Filed: Feb. 1, 2008

(86) PCT No.: PCT/FI2008/050038
§ 371 (c)(1),
(2), (4) Date: Aug. 11, 2009

(87) PCT Pub. No.: WO2008/093002
PCT Pub. Date: Aug. 7, 2008

(65) Prior Publication Data
US 2010/0081139 A1    Apr. 1, 2010

Related U.S. Application Data

(60) Provisional application No. 60/905,917, filed on Mar. 9, 2007.

(30) Foreign Application Priority Data

Feb. 1, 2007  (FI) ..................................... 20070082
Mar. 9, 2007  (FI) ..................................... 20070203

(51) Int. Cl.
C12Q 1/68 (2006.01)
C12P 19/34 (2006.01)
C07H 21/02 (2006.01)
C07H 21/04 (2006.01)

(52) U.S. Cl. ....... 435/6.1; 432/91.2; 536/23.1; 536/24.3

(58) Field of Classification Search ............... 435/6, 7.1, 435/91.2; 536/23.1, 24.3
See application file for complete search history.

(56) References Cited

U.S. PATENT DOCUMENTS

| | | | |
|---|---|---|---|
| 5,716,784 A | 2/1998 | Di Cesare | 435/6 |
| 5,756,709 A | 5/1998 | Nelson | 536/24.3 |
| 5,928,862 A * | 7/1999 | Morrison | 435/6.18 |
| 6,103,476 A | 8/2000 | Tyagi et al. | 435/6 |
| 2003/0022177 A1 | 1/2003 | Wittwer et al. | 435/6 |
| 2003/0143591 A1 | 7/2003 | Davies et al. | 435/6 |
| 2004/0014119 A1 | 1/2004 | Itoh et al. | 435/6 |
| 2004/0029119 A1 | 2/2004 | Nurmi | 435/6 |
| 2006/0029965 A1 | 2/2006 | Wittwer et al. | 435/6 |
| 2006/0057650 A1* | 3/2006 | Dahm | 435/7.23 |
| 2006/0127940 A1* | 6/2006 | Bao et al. | 435/6 |
| 2006/0134644 A1 | 6/2006 | Hartel et al. | 435/6 |
| 2006/0240409 A1* | 10/2006 | Prince et al. | 435/5 |

FOREIGN PATENT DOCUMENTS

| | | |
|---|---|---|
| EP | 0232967 | 8/1987 |
| WO | WO 01/61034 | 8/2001 |
| WO | WO2005/118144 | 12/2005 |

OTHER PUBLICATIONS

Tyagi et al. Nature Biotechnology 16 : 49 (1998).*
*Hagren et al, "An automated PCR platform with homogeneous time-resolved fluorescence detection and dry chemistry assay kits," 374 *Analytical Biochem.* 411 (2007).
*Tani et al, "Quantification of genetically modified soybean by quenching probe polymerase chain reaction," 53 *J Agricultural and Food Chem.* 2535 (2005).
*Tani et al, "Quantitative method for specific nucleic acid sequences using competitive polymerase chain reaction with an alternately binding probe," 79 *Analytical Chem.* 974 (2006).
*Morisson et al, "Solution-Phase detection of polynucleotides using interaction fluorescent labels and competitive hybridization," 183 *Analytical Biochem.* 231 (1989).
*Pryor et al, "Real-time polymerase chain reaction and melting curve analysis," 336 *Methods in Molecular Biology.* 19 (2006).
*Kim et al, "Rapid genotypic detection of *Bacillus anthracis* and the *Bacillus cereus* group by multiplex real-time PCR melting curve analysis," 43 *FEMS Immunology and Medical Microbiology.* 301 (2005).
*Von Lode et al, "Fully automated, homgeneous nucleic acid detection technology based on dry-reagent assay chemistry and time resolved fluorometry," 53 *Clin Chem.* 2014 (2007).
*Rissanen et al, "Novel homogenous time-resolved fluorometric RT-PCR assays for quantification of PSA and hK2 mRNAs in blood," 40 *Clin Biochem.* 111 (2006).
*Kiviniemi et al, "A homogeneous high-throughput genotyping method based on competitive hybridization," 36 *Clin Biochem.* 633 (2003).
Sanchez et al., "Two-temperature LATE-PCR Endpoint Genotyping," 6 *BMC Biotechnol.* 44 (2000).

* cited by examiner

Primary Examiner — Ethan C Whisenant
(74) *Attorney, Agent, or Firm* — James C. Lydon

(57) ABSTRACT

A method for detecting the presence of a target polynucleotide in a sample, including providing a mixture of the sample and target binding agent and measuring a signal from the mixture, where the target binding agent is capable of assuming a first position where the target binding agent is not bound to the target polynucleotide and a second position where the target binding agent is bound to the target polynucleotide, and the intensity of the signal depends on the proportion of target binding agent in the first and second positions. The method is suitable for detecting a PCR product using a homogeneous detection method.

21 Claims, No Drawings

METHOD FOR DETECTION OF PRESENCE OF TARGET POLYNUCLEOTIDE IN SAMPLES

This application is a National Stage of International Application PCT/FI2008/050038, filed Feb. 1, 2008, which claims benefit under 35 U.S.C. §119 of U.S. provisional application 60/905,917, filed Mar. 9, 2007, Finnish patent application 20070082, filed Feb. 1, 2007, and Finnish patent application 20070203, filed Mar. 9, 2007.

FIELD OF THE INVENTION

The present invention relates to a method for detection of the presence of a target polynucleotide in a sample. More particularly the present invention relates to a method for detection of a nucleic acid amplification product by using a homogenous detection method.

BACKGROUND OF THE INVENTION

The publication and other material used herein to illuminate the background of the invention, and in particular, cases to provide additional details respecting the practice, are incorporated by reference.

The polymerase chain reaction (PCR) (Saiki et al., 1985 Science 230, 1350-1354) is a nucleic acid amplification technique that has become the most important nucleic acid diagnostic tool. It enables extremely sensitive detection of specific nucleic acid sequences in various sample matrices. To find out whether or not a sample contains e.g. a specific pathogen, the sample can be analyzed for the presence of a nucleic acid specific to the pathogen by PCR. If, using oligonucleotide primers specific for the nucleic acid of the pathogen of interest, a PCR product can be amplified starting from nucleic acids extracted from the sample, the sample is likely to contain the pathogen of interest. Since PCR can, at least in theory, amplify even one target DNA molecule up to a detectable level, it allows extremely sensitive detection of pathogens, mutations, cancer cells and other targets that can be identified by specific nucleic acid sequences. In order for the assays to function, all PCR tests require a method for reliable and accurate detection and identification of the PCR product. The first diagnostic tests based on PCR were quite cumbersome and not amenable to large scale screening methods, since the PCR detection methods were not very straightforward. Several post PCR steps, such as restriction enzyme analysis, agarose gel electrophoresis or heterogeneous hybridization assays were needed to confirm the identity of the PCR product. These methods require that the reaction vessels in which PCR is performed are opened after amplification, which constitutes a serious risk of contamination and consequent false positive PCR results. To overcome the problems associated with manipulation of PCR products, fluorescent techniques and assay formats have been developed that greatly simplify the protocols used for the detection of specific nucleic acid sequences. These methods, exemplified e.g. in U.S. Pat. Nos. 5,994,056, 5,804,375, EP0543942, EP0232967, US2003143591, US2003022177, US2004029119, EP0912760 and by Sanchez J. et al. in "Two-temperature LATE-PCR endpoint genotyping", published in BMC Biotechnology, vol. 6, December 2006, involve the detection of a specific PCR product in a homogeneous solution without the need to open the amplification tubes after PCR. The results can be read in real time as the PCR product is accumulated or at the end of the thermal cycling protocol directly from the closed amplification wells.

The principle of real-time PCR is described e.g. in U.S. Pat. No. 5,994,056. In real-time PCR, fluorescence generated by an intercalating dye or by a homogeneous probe-based detection system is measured more than once during PCR amplification. Typically, the first measurement or measurements are performed in the beginning or even prior to target amplification to determine the baseline signal of the reaction. To determine whether or not the target sequence is amplified, fluorescent signal intensities obtained later during amplification or after amplification has been completed are compared to the baseline and, if a significant change—an increase or a decrease, depending on the detection method that is used—is detected, the reaction is considered to be positive, i.e. to contain the sequence of interest. On the other hand, if there is no significant change in the intensity of the signal recorded from the reaction, the reaction is considered negative i.e. not to contain the sequence of interest. In essence, real-time PCR is thus based on detecting a change in signal intensity, said change being caused by the appearance of the specific PCR product. The clear benefit of the method is that a reaction-specific baseline level can be determined to which all subsequent signal intensities can be compared. This makes the technique very sensitive. However, in the measurement of a change in fluorescence lies a problem: changes in fluorescence intensity can be caused by artifacts that are not related to the specific amplification reaction. For example, a leaking reaction vessel lid or appearance of bubbles in the reaction solution during thermal cycling can cause significant changes in the measured signals without any relation to the amplification process. Also, it may be difficult to detect the specific change in signal in the presence of a lot of background fluorescence. Such unspecific effects on fluorescence intensity can, in the worst case, result in false results.

Instead of using the real-time measurement technique, one can also determine whether or not a specific nucleic acid sequence has been amplified by performing a measurement after completion of the amplification protocol, provided that the reaction mixture includes an intercalating dye or a probe system capable of reporting the presence of a specific target sequence. In such end-point assays it is common practice to analyze negative control reactions in parallel with the actual samples. The negative control reactions are usually prepared by adding water instead of a template nucleic acid to an amplification mixture—therefore, no amplification of the target nucleic acid takes place in the negative control reactions. Thus, the negative control reactions are used to determine the baseline signal that is characteristic for the batch of analytical results—it therefore plays the role in end-point assays that the initial baseline measurements have in the real-time technique. Negative control reactions need to be included in each analytical run since the fluorescence background emitted by individually prepared reaction mixtures varies to some extent and, even more importantly, the absolute signal levels recorded by individual fluorescence measurement instruments varies. Therefore, it is not possible to determine a general background level that would be applicable in all instruments at all times. To determine whether or not a sample contains the sequence of interest, the signal emitted by the sample reaction is compared to the negative controls. If a significant difference is detected between the signals emitted by the sample reactions and the negative control reactions, the sample is considered positive. On the other hand, if the sample reaction gives a signal intensity that is essentially the same as the signal given by the negative control reactions, the sample is considered negative. Therefore, this method is also based on detecting a change in fluorescence intensity—the main difference between this technique and the real-time technique is that while in the real-time method the baseline is determined for each reaction individually, in the end-point method a common baseline is determined for all simultaneously analyzed samples using negative control reactions that are run in parallel with the sample reactions. Just like in the real-time method, false results can be caused by unspecific sources of fluorescence change that may take place in the negative control reactions or in the sample reactions. Furthermore, results can be distorted by differences in the background signal emitted by individual samples: if, for example, a particular sample contains a colored substance that affects the fluorescence emitted by the fluorophores utilized in the detection method, false results can be obtained. Another important source of errors is that the method is very sensitive to the exact reaction volume—even slight changes in reaction volume can distort the results if individual control and sample reactions contain slightly different amounts of fluorescent label to begin with.

One solution to unspecific changes in fluorescence intensity caused by differences in reaction volume has been described in U.S. Pat. No. 5,928,907. In the method described in U.S. Pat. No. 5,928,907 each reaction contains—in addition to a first fluorescent indicator, the signal intensity of which is related to the amount of PCR product present in the reaction—a second fluorescent indicator, which is a label molecule the signal intensity of which is essentially independent of the amount of PCR product present in the reaction. Instead, the signal intensity of the second fluorescent indicator depends on the reaction volume in a similar manner as the first fluorescent indicator. Therefore, by recording at each measurement the signals of both fluorescent indicators, it is possible to eliminate the unspecific effects on signal intensities caused by differences in reaction volume by correcting the signals of the first fluorescent indicator by calculating the relationship between the signals given by the first and second fluorescent indicators. While this method has found wide acceptance and applications in the art, it has the intrinsic problem that the second fluorescent indicator as such increases the total fluorescence background of the reaction and reduces the possibilities for multiplexing. In this context, multiplexing means the art of combining the amplification and detection reactions of several different target nucleic acids in one PCR reaction. If a second fluorescent indicator according to U.S. Pat. No. 5,928,907 is used, the spectral area of the second fluorescent indicator is reserved, leaving less room for other fluorescent indicators allowing the detection of other target sequences in the same reaction. That is, if one has access to nine different spectrally resolvable labels, one can maximally only amplify and detect eight different targets simultaneously, if one of the labels has to be used as a second fluorescent indicator. It would be desirable to be able to combine as many targets as possible in one reaction—therefore, it would be advantageous if the second fluorescent indicator was not needed.

Therefore, due to the problems associated with the existing techniques, there is a need for a method that would allow the detection of a PCR product without the need to resort to real-time measurement, negative control reactions or a second fluorescent indicator dye. These problems are solved with the methods of the present invention.

OBJECT AND SUMMARY OF THE INVENTION

An object of the present invention is to provide a method for detection of the presence of a target polynucleotide in a sample.

Thus the present invention provides a method for detection of the presence of a target polynucleotide in a sample. The method comprises a) providing a mixture of said sample and target binding agent, said target binding agent being capable of assuming a first position where said target binding agent is not bound to said target polynucleotide and a second position where said target binding agent is bound to said target polynucleotide, and a signal is measurable from said mixture, the intensity of said signal depending on the proportions of target binding agent being in said first and second positions;

b) exposing at least once said mixture to a first condition resulting in that said target binding agent is in said first position;

c) exposing at least once for a prolonged time said mixture to a second condition where said target binding agent is capable of assuming the second position, d) measuring at least once after said mixture has been exposed to said first condition said signal of the mixture at a time when less than in the step e) of said target binding agent present in said mixture has assumed the second position;

e) measuring at least once, after said mixture has been exposed to said second condition, said signal of the mixture at a time when, if the sample contains said target polynucleotide, more than in step d) of said target binding agent has assumed the second position; and f) determining the relationship of the measurement results obtained in steps d) and e) and comparing it to a predetermined cut-off value that is characteristic for said mixture of sample and target binding agent to determine whether said target polynucleotide is present in the sample or not.

DETAILED DESCRIPTION OF THE INVENTION

The present invention relates to a homogeneous method for the detection of a target polynucleotide. The term "homogeneous" method, as used herein, refers to a separation-free assay method in which the assay can be performed without any washing, chromatographic or other physical separation steps to distinguish between signals coming from bound and free molecular assay components.

Typical for the method of the present invention is that it can be performed without having to resort to real-time monitoring of nucleic acid amplification, negative control reactions or a second fluorescent indicator dye. The method is based on providing a reaction mixture that contains, in addition to the target polynucleotide to be detected, reagents for homogeneous detection of the target polynucleotide. There are several methods known in the art that allow homogeneous detection of a target polynucleotide, any of which could in principle be used according to the present invention. In a preferred embodiment of the present invention, the homogeneous detection is based on labeled hybridization probes. These are oligonucleotides or oligonucleotide analogs conjugated to labels, which are usually fluorophores. Suitable oligonucleotide analogs include but are not limited to oligonucleotides containing at least one residue of locked nucleic acid or peptide nucleic acid. Preferably, the homogeneous detection is based on competitive hybridization (EP0232967B1) or on a probe that is labeled with two labels, one of which is capable of absorbing or quenching the signal emitted by the other label when the probe is not hybridized to a target sequence. Examples of such probes have been described in the literature, e.g. in U.S. Pat. Nos. 5,925,517, 6,103,476, 6,150,097 and EP0792374B1.

One embodiment of the present invention provides a method for detection of the presence of a target polynucleotide in a sample wherein a mixture of said sample and target binding agent is provided, said target binding agent being capable of assuming a first position where said target binding agent is not bound to said target polynucleotide but instead is free and a second position where said target binding agent is bound to said target polynucleotide.

Another embodiment of the present invention provides a method for detection of the presence of a target polynucleotide in a sample wherein the mixture further comprises a second binding agent and the target binding agent is capable of assuming a third position where said target binding agent is bound to said second binding agent, and a single target binding agent cannot simultaneously be in the second and third positions and a signal is measurable from said mixture, the intensity of said signal depending on the proportions of target binding agent being in said first, second and third positions and in step e) the signal is measured at least once after said mixture has been exposed to said second condition at a time when, if the sample contains said target polynucleotide, more than in step d) of said target binding agent has assumed the second or the third position.

The term "position" as used herein refers to a state of a molecule. Alternative positions of a molecule can be defined as states in which said molecule is or is not bound by at least one covalent or non-covalent bond to another molecule. For example, in the context of the present invention, if a labeled oligonucleotide probe is said to be in the "first position" as the term is used herein, said labeled oligonucleotide is not part of a stable base-pairing interaction with a target nucleic acid or stably bound to a second binding agent but is instead free in solution and only interacts transiently with other molecules or molecular complexes that are free in solution. In contrast, if said labeled oligonucleotide is in a "second position" or in a "third position" as the terms are used herein, said labeled oligonucleotide is base-paired to a target polynucleotide or bound to a second binding agent, respectively.

The term "target binding agent" as used herein refers to any substance or complex of substances that is capable of forming a complex with the target polynucleotide. The target polynucleotide is the polynucleotide of interest, the presence and/or quantity of which is being measured. In another embodiment there are more than one target polynucleotides, such as 1-5 or even 5-10 or even more than 10, each of them having their own specific target binding agent and all of them are detected in the same reaction. Generally this means that each target binding agent may be labeled with labels having different colors or other distinguishable characteristics, and several targets are detected in the same mixture. Examples of suitable target binding agents include but are not limited to nucleic acids, such as polynucleotides, oligonucleotides and labeled oligonucleotides; nucleic acid analogs, such as oligonucleotides or labeled oligonucleotides containing at least one residue of locked nucleic acid, peptide nucleic acid or phosphothioate nucleic acid; nucleic acid binding chemicals; intercalating dyes such as ethidium bromide or SYBR Green; proteins such as antibodies; and metal ions such as terbium ions. A person skilled in the art would understand that the examples referred to can also be suitable second binding agents.

The method of the present invention is suitable for use in a PCR reaction. The PCR reaction may be carried out by using any known thermal cycler that is suitable for controlling the temperature of the reagents included in the mixture of sample and target binding agent and, in some embodiments, second binding agent. In a preferred embodiment, the thermal cycler further comprises a measurement unit, preferably a fluorescence or time-resolved fluorescence measurement unit that is arranged to record the signals emitted by reaction mixtures contained in reaction vessels situated inside the instrument. In one embodiment the target polynucleotide is a PCR product, which may be detected directly from the PCR reaction mixture or alternatively a sample of the mixture may be taken and analyzed separately. When the target polynucleotide is a PCR product, the target binding agent may be included in the PCR amplification mixture prior to amplification. Alternatively, the target binding agent can be added to the amplification mixture after completion of amplification or during amplification.

In one embodiment the mixture of sample and target binding agent further comprises nucleic acid amplification reagents. The term "nucleic acid amplification reagent" refers to any substance that can be used as a component in a reaction that can result in the amplification of one or more nucleic acid molecules. Typical examples of nucleic acid amplification reagents include but are not limited to nucleic acid polymerases, such as DNA and RNA polymerases; nucleotides; oligonucleotides; salts, such as magnesium chloride, potassium chloride and sodium chloride; DMSO; betaine; bovine serum albuim; sugars: glycerol; detergents, such as Triton X-100 and Tween-20. One example of supplying the nucleic acid amplification reagents is the dry chemistry principle described in WO2005118849. There are several methods of nucleic acid amplification known in the art and any such method can be used in the scope of the present invention. Suitable methods for nucleic acid amplification include but are not limited to the polymerase chain reaction (PCR), nucleic acid sequence based amplification (NASBA), transcription mediated amplification (TMA), strand displacement amplification (SDA), Q beta replicase amplification, reverse transcriptase polymerase chain reaction (RT-PCR), ligase chain reaction (LCR), rolling circle amplification (RCA), proximity ligation assay and immuno-PCR assay.

In another embodiment said mixture is exposed to conditions that allow nucleic acid amplification to occur in said mixture and said detection is carried out after completion of said amplification, when no more amplification takes place in the mixture. In still another embodiment said mixture is exposed to conditions that allow nucleic acid amplification to occur in said mixture and said detection is carried out at least once during said amplification.

A signal is measurable from said mixture and the intensity of said signal depends on the proportions of target binding agent being in said first and second positions. The term "signal" as used herein refers to a measurable output. For example, in one embodiment the signal is an optical signal. The term "optical signal" as used herein refers to a signal measurable as emitted, absorbed or reflected light. Any luminescent or radioactive output shall be understood as a signal according to the present invention. Examples of signals according to the present invention include, but are not limited to, fluorescence signal; time-resolved fluorescence signal; absorbance; fluorescence polarization; luminescent signal; and radioactive signal. Other suitable forms of signal include but are not limited to a surface plasmon resonance signal.

The signal may be measured by using any suitable method, such as by time-resolved fluorometry. In time-resolved fluorometry, the emission intensity of a sample is measured after single, consecutive excitation pulses. The excitation flash time is typically 1 to 10 μs. Emission is measured with a photomultiplier tube by photon counting. After a certain delay from excitation, photon counting is initiated by electronic gating. The flash frequency, the total measurement time as well as the delay and counting times can be varied, but normally the total measurement time is 1 or 2 s comprising 1000 individual cycles during which the total photon amount is counted. Time-resolved fluorometry is widely used in bio-affinity assays together with labels having a long decay time (Lövgren, T. and Pettersson, K. (1990) Time-resolved fluoroimmunoassay, advantages and limitations. In Van Dyke, K. (ed.), Luminescence immunoassay and molecular applications. CRC Press, Boca Raton, Fla., 933-250). The choice of method for measuring the intensity of said signal depends on the labels that are used in the method. If time-resolved fluorometry is used, then the labels in the assay are preferably fluorophores with long excited state lifetimes, such as lanthanide chelates or lanthanide cryptates or other fluorophores with long excited state lifetimes. Besides time-resolved fluorometry, it is possible to use, depending on the label or labels that are used in the assays, other methods for measuring the intensity of said signal. Examples of suitable measurement technologies include but are not limited to fluorometry, chemiluminescence, electrochemiluminescence, bioluminescence, phosphorescence, radioactivity measurement, surface plasmon resonance, fluorescence polarization, absorbance and anti-Stokes fluorometry. It will be appreciated by those skilled in the art that any combination of label and measurement technique that allows homogeneous detection of nucleic acid hybridization is suitable for use when performing the method of the present invention. In a preferred embodiment, the signal is measured directly from a closed reaction vessel that contains the mixture of sample and target binding agent and, in some embodiments, second binding agent. Suitable reaction vessels include but are not limited to plastic reaction tubes such as PCR tubes, glass capillaries and microcentrifuge tubes. A preferred reaction vessel has the characteristics of the reaction vessel described in WO2005118144.

Typically said mixture is exposed to a first condition where said target binding agent is in said first position and then it is exposed to a second condition where said target binding agent is capable of assuming the second position. The terms "first condition" and "second condition" as used herein refer to physical and/or chemical conditions that prevail in the solution that comprises said mixture. When the mixture is "exposed to" a first or second condition, i.e. the first or second condition prevails in the reaction mixture, or the mixture is just about to reach said first or second condition. When the mixture is "just about to reach" a first or second condition, the condition that prevails in the mixture is changing and approaching the defined first or second condition. For example, if the second condition is defined as a temperature of 50° C., the temperature of the mixture, when it is exposed to the second to the second condition, as the term is used herein, is either 50° C. or is at least approaching 50° C. The "first condition" is defined as a physical and/or chemical state at which said target binding agent can assume said first position, i.e. it is not capable of forming a covalent or non-covalent bond with the target polynucleotide or with the second binding agent. The "second condition" is defined as a physical and/or chemical state at which said target binding agent is capable of forming a covalent or non-covalent bond with said target polynucleotide or with a second binding agent. However, it is also possible, when the "second condition" prevails, that said target polynucleotide is in said first position—it is capable of assuming the second or third position but does not necessarily do so, i.e. it can also assume the first position. In one embodiment the first and the second conditions are achieved by heating and by cooling. In these embodiments the temperature of the first condition is essentially higher or lower, preferably higher than that of the second condition. "Essentially higher or lower" referring, in this context, to that the difference in temperature is at least 10° C., preferably at least 20° C., more preferably at least 40° C. and most preferably at least 80° C. In another embodiment the first and the second conditions are achieved chemically. If the first and/or second conditions are "achieved chemically" as the term is used herein, said first or second condition is at least partly defined by the chemical composition of the reaction mixture. A first condition achieved chemically is e.g. a solution in which the concentration of positively charged ions is too low to allow nucleic acid hybridization to occur. An example of a second condition is a solution in which the concentration of positively charged ions, such as magnesium ions, is high enough to allow nucleic acid hybridization to occur. A first or second condition can be achieved by denaturing with a chemical base or by neutralizing with a chemical acid. In yet another embodiment the first and the second conditions are achieved by adjusting the concentration of ions in said mixture of sample and target binding agent and, in some embodiments, second binding agent. It will be appreciated by those skilled in the art that many different methods exist and are known in the art for denaturing and renaturing nucleic acids. In principle, all such methods can be used to achieve said first and second conditions.

In PCR reaction the first condition refers to the situation where the probes and target polynucleotides are in denatured state and not hybridized. In practice the reaction mixture may be heated to achieve the first condition. In the second condition the temperature has been lowered and the probes are hybridized with target polynucleotides.

Typically the signal is measured in a first measurement from the mixture soon after having exposed the mixture being in the first condition to the second condition at a time when less than in a second, typically subsequent, measurement step of said target binding agent present in said mixture has assumed the second position. In one embodiment the signal is measured from the mixture at a time when substantially none of said target binding agent present in said mixture has assumed the second position. "Substantially none" as used herein refers to a level which is lower than in the second measurement if the sample contains the target polynucleotide. Preferably, the signal is measured less than 30 seconds or even more preferably less than 10 seconds after said mixture has been exposed to the second condition. For example, the mixture can first be heated to denature all nucleic acids and then cooled down to a temperature where the target binding agent is capable of assuming said second position with the target polynucleotide and then, just when the lower temperature has been reached, preferably less than 30 seconds after reaching the lower target temperature or even slightly before reaching the lower target temperature, the first measurement can be performed. Typically, when the first measurement is performed, practically all of the target binding agents are still in said first position, i.e., if the target binding agent is a labeled oligonucleotide probe, said probe molecules are not hybridized. Suitably, more than 25%, more preferably more than 50% of the target binding agents are still in said first position, e.g. denatured, when the first measurement takes place.

Typically said signal is measured from the mixture for a second time, referred to as the second measurement, at a time when more than in the previous measurement step of said target binding agent has assumed the second position if the sample contains said target polynucleotide. If the sample does not contain the target polynucleotide, the second measurement is measured at a the time when more than in the previous step of said target binding agent could have been able to assume said second position, had the target polynucleotide been present. Preferably, the second measurement takes place at least 1 second, more preferably at least 30 seconds after the first measurement. If the mixture does not contain any target polynucleotide, typically 100% of target binding agent is still in said first position when the second measurement takes place. The more target polynucleotide is present in the mixture, however, the larger proportion of target binding agent has assumed the second position when the second measurement takes place. For example, if the mixture contains 10 times more target polynucleotide than target binding agent, typically more than 50%, even about 100% of target binding agent is in said second position when the second measurement takes place. In one embodiment said signal is measured from the mixture for a second time at a time when substantially all of said target binding agent has assumed the second position if the sample contains said target polynucleotide.

It should be understood that in all embodiments of the invention at least two measurements of the signal are made:

In at least one measurement, referred to as the first measurement, the measurement is made soon after having exposed said mixture to a first condition resulting in that the binding agent is in the first position at the time of the measurement. Typically the measurement is made when the mixture is exposed to the second condition. Accordingly the mixture is in, or is about to reach, the second position. In some preferred embodiments the measurement is made when the mixture is in the second condition. If the measurement is made when the mixture is about to reach the second condition it should be understood that the divergence of the condition of the mixture from the second condition in relation to the parameter or parameters changed between the first condition and second condition should not diverge from the values of the second condition more than 75%, preferably more than 50%, more preferably more than 25% and most preferably more than 10% of the difference in the parameter values between the first and second positions. The mixture typically needs to be exposed to the first condition for not more than 5 minutes, preferably for not more than 1 minute, more preferably for not more than 10 s and most preferably for not more than 2 s before measurement. When referring to that the binding agent is in the first position at the time of measurement it is to be understood that typically at least 50%, preferably at least 65%, more preferably at least 80%, even more preferably at least 90% and most preferably about 100% of the binding agent is in the first position. Typically "soon after" would refer to that not more than 90 s, preferably not more than 30 s, more preferably not more than 10 s and most preferably not more than 3 s has passed after having exposed the mixture to the first condition before the measurement.

In at least another measurement, referred to as the second measurement, the measurement is made when the mixture has been exposed to the second condition. In this measurement at least more than in the first measurement of the binding agent is in the second position provided that the sample contains the target polynucleotide. This situation is typically achieved by exposing the mixture for a prolonged time to the second condition. In this context the term "prolonged time" refers to that the mixture has been exposed to the second condition long enough for at least some of the target binding agent having reached second or third position if the sample contains said target polynucleotide. Typically at least 3%, preferably more than 10% and more preferably more than 30% and most preferably more than 90% of the target binding agent is in the second or third position. In any case more of the target binding agent is in second or third position in the second measurement than in the first measurement. In a typical embodiment the prolonged time exposed to the second condition is longer than in case of the first measurement.

It should be understood, that although the measurements are referred to as the first and the second measurements they need not be carried out in respective order, i.e. the second measurement can be carried out before the first measurement, although in many preferred embodiments the first measurement is carried out before the second one. It should further be understood that more than two measurements can be carried out. Accordingly the invention also comprises embodiments where more than two measurements are carried out as long as two of the measurements are in accordance with what is defined above.

It should further be understood, that it is not essential to which conditions the mixture is exposed when the at least two measurements referred to above are made although both measurements are typically made when the mixture is exposed to the second condition. Essential is that the mixture has been exposed to the first and second conditions before corresponding measurements to enable at least two measurements with signals corresponding to signals representing mixtures with a different proportion of target binding agent having assumed the second or third position.

Finally the relationship of the values of the signal intensities obtained as results of the measurement steps is determined and compared to a pre-determined cut-off value that is characteristic for said mixture of sample and target binding agent. The term "relationship" as used herein refers to a mathematical relationship between the two measured numerical values. In one embodiment, said relationship is determined by calculating the difference of the measured signal intensity values. In a preferred embodiment, said relationship is determined by calculating the ratio of the measured signal intensity values. This ratio is used to determine whether said target polynucleotide is present in the sample or not. The actual percentages of target binding agent being in the first and in the second positions in the measurements is not essential as far as the same conditions are used to perform the measurements required to determine the cut-off value and to perform the measurements needed to determine the ratio of signals for the actual samples. In any case the difference in the amounts of target binding agent being in the first and in the second positions in said two measurements should be adequate to enable the determination of the ratio. For each combination of target polynucleotide and target binding agent and, in some embodiments, second binding agent, it is possible to find optimal conditions for performing the measurements to get as big a difference between the ratio of signals for a mixture that does not contain any target polynucleotide and a mixture that does contain target polynucleotide. Generally, the optimal conditions are such that when the first measurement is carried out, a maximal amount of target binding agent is in the first position and when the second measurement is carried out, a maximal amount of target binding agent can be in the second and/or, in some embodiments, in the third position. To define the optimal conditions for performing the method of the present invention using a particular combination of target polynucleotide, target binding agent and, in some embodiments, second binding agent, one has to define 1) the exact manner in which the first condition and second condition are achieved and 2) the points of time when the first and second measurements are carried out and 3) the concentrations of target binding agent and, in some embodiments, second binding agent and 4) the concentrations of other components of said mixture, which components may include but are not limited to buffer components, ions, detergents, stabilizers and proteins.

The cut-off value can be determined in many ways. In one embodiment of the present invention, the whole assay is performed using dry reagent PCR. In dry reagent PCR all PCR reagents, including target specific labeled oligonucleotide probes which can be understood as the target binding agent and second binding agent of the present invention, are dispensed and dried onto reaction vessels. The principle of dry reagent PCR has been described in WO2005118849. When a batch of dry reagent vessels has been prepared, the cut-off value can be determined by:

1) Taking a representative number of dry reagent PCR reaction vessels belonging to the manufacturing lot for which a cut-off is to be determined. The taken vessels are referred to as background controls. For example, one can take 1% of all dry reagent vessels belonging to the manufacturing lot.
2) Reconstituting the reagents dried onto the background controls with sterile water.
3) Determining the said ratio of signals (H/D) for each background control.
4) Calculating the average H/D (M) and standard deviation (SD) of all background controls representing the manufacturing lot for which a cut-off is to be determined.
5) Determining the cut-off as M+ nSD, where n can be chosen to give the desired level of accuracy. Typically, n has a value between 1 and 10, preferably 2, 3 or 4.

In another embodiment of the method of the invention there is also a second binding agent and the target binding agent is capable of assuming a third position where said target binding agent is bound to said second binding agent, and a single target binding agent cannot simultaneously be in the second and third positions and a signal is measurable from said mixture, the intensity of said signal depending on the proportions of target binding agent being in said first, second and third positions and in the second measurement step the signal is measured for second time at a time when more than in the previous measurement step of said target binding agent has assumed the second or the third position. In one embodiment the signal is measured for second time at a time when substantially all of said target binding agent has assumed the second or the third position if the sample contains said target polynucleotide. The term "second binding agent" as used herein refers to a chemical moiety capable of forming a molecular complex with the target binding agent under at least said second conditions. In one embodiment of the present invention, the target binding agent and second binding agent are mutually complementary labeled oligonucleotides conjugated to labels that, when brought into close proximity by hybridization between the target binding agent and the second binding agent, interact with each other in a manner that affects at least the signal emitted by one of the labels. In a preferred embodiment, the target binding agent is an oligonucleotide probe labeled with a fluorescent label and the second binding agent is an oligonucleotide labeled with a quencher label that is capable of quenching the fluorescence of the label attached to the target binding agent when brought into close proximity with the target binding agent, such as when the target binding agent is hybridized with the second binding agent.

Then said mixture is exposed to a second condition where said target binding agent is capable of assuming the second and the third position, the proportion of target binding agent being in the second and third positions depending on the amount of target polynucleotide in said mixture.

Said signal is measured from the mixture at a time when less than in the second measurement step of said target binding agent present in said mixture has assumed the second or the third position. In one embodiment the signal is measured from the mixture at a time when substantially none of said target binding agent present in said mixture has assumed the second or the third position.

Said signal is measured from the mixture another time at a time when more than in the previous measurement step of said target binding agent has assumed the second or the third position, and the relationship of the signals obtained is used to determine whether said target polynucleotide is present in the sample or not, as described above. In one embodiment said signal is measured from the mixture another time at a time when substantially all of said target binding agent has assumed the second or the third position.

In one embodiment the target binding agent is a nucleic acid. In another embodiment the target binding agent is an intercalating dye. In still another embodiment the target binding agent is a labeled oligonucleotide, such as an oligonucleotide labeled with at least one fluorophore. In still another embodiment the target binding agent is an oligonucleotide labeled with at least two different kinds of labels, which labels are capable of interacting with each other when brought to close proximity with each other. Suitable forms of interaction include but are not limited to fluorescence resonance energy transfer (FRET) and fluorescence quenching. Any form of interaction that causes a difference in said measurable signal intensity when the target binding agent is in said first, second or third positions, shall be understood as an interaction as the term is used herein.

In one embodiment there are more than one target polynucleotides, such as 1-5 or even 5-10, each of them having their own specific target binding agent and all of them are detected in the same mixture. Generally this means that each target binding agent may be labeled with labels having distinguishable signals, and several targets may be detected at once. In such an embodiment, each target polynucleotide may also have their own specific second binding agent. Alternatively, in another embodiment, each target polynucleotide has its own specific target binding agent but only one second binding agent is included in the mixture, said second binding agent being capable of binding only one target binding agent or, alternatively, said second binding agent can be selected so that it is capable of binding more than one, preferably all different target binding agents present in the same mixture. The term "kind of" as used herein refers to the molecular composition of the substance. Thus, e.g. "more than one kind of target binding agent" refers to a mixture of at least two target binding agents the molecular compositions of which are not identical with each other and "one kind of target polynucleotide" means a target polynucleotide that has a defined molecular composition.

The labels to be used in accordance of the present invention include any suitable label known in the art. The term "label" as used herein refers to a chemical moiety that is covalently or non-covalently conjugated to a second molecule with the purpose of conferring to said second molecule a detectable characteristic of the label moiety. Examples of such labels include but are not limited to enzymes, (e.g. alkaline phosphatase and horseradish peroxidase) and enzyme substrates, radioactive atoms, fluorophores, light absorbing groups such as dark quenchers [e.g. dabcyl, Black Hole Quenchers (Biosearch technologies), QSY7], lanthanide labels including lanthanide chelates and lanthanide cryptates, chromophores, chemiluminescent labels, electrochemiluminescent labels, ligands having specific binding partners or any other labels.

The term "fluorophore" as used herein refers to any moiety that emits light upon excitation with light. Examples of suitable fluorophores include but are not limited to prompt fluorophores such as 6-carboxyfluorescein (FAM), tetramethylrhodamine, TAMRA, HEX, TET, JOE, VIC, EDANS and ROX, green fluorescent protein and other fluorescent proteins, fluorescent nucleotides and nucleotide derivatives and analogs; labels with long emission lifetimes such as lanthanide chelates and lanthanide cryptates, preferably europium, terbium, samarium and dysprosium chelates and cryptates; luminescent particles including but not limited to luminescent particles having a diameter of less than 10 μm. One embodiment of the present invention provides a device arranged to and having means to carry out any method of the invention. For example said device is programmed to control the reaction, such as to expose the sample to the first and the second conditions, to measure the signals, to calculate and determine the ratio of the signals measured and to determine the presence of the target polynucleotide in the sample according to any of the methods of the invention. "Device" as used herein may refer to a single integrated device capable of carrying out all the acts required or a device arrangement, which comprises e.g. a device for handling the sample, a measuring unit and a computing unit, such as a computer or an integrated computing unit. The device arrangement may contain a computer-readable data storage medium having computer-executable program code stored, which is operative to perform the controlling, measuring and calculating steps of the method of the invention when executed on the computing unit, or a computer system, which is programmed to perform the controlling, measuring and calculating steps of the method of the invention. Example of such device is a thermal cycler of a PCR instrument that has an integrated fluorescence or time-resolved fluorescence measurement unit and associated software, the device being capable of performing the methods of the present invention. In one embodiment of the present invention the device is a so-called random access nucleic acid analyzer that is capable of receiving new samples for analysis at any time, even when other samples are being analyzed. In another embodiment of the present invention the device is a so-called batch analyzer into which new samples can be inserted for analysis when the analysis of a previous batch of samples is finished.

In some especially preferred embodiments of the method of the invention a first label is incorporated in the target binding agent and a second label is incorporated in the second binding agent and said first and second labels are capable of interacting with each other when the target binding agent is in said third position.

Some embodiments of the invention relate to a method comprising
a) providing a mixture of said sample and target binding agent, said target binding agent being capable of assuming a first position where said target binding agent is not bound to said target polynucleotide and a second position where said target binding agent is bound to said target polynucleotide, and a signal is measurable from said mixture, the intensity of said signal depending on the proportions of target binding agent being in said first and second positions;
b) exposing said mixture to a first condition where said target binding agent is in said first position;
c) exposing said mixture to a second condition where said target binding agent is capable of assuming the second position;
d) measuring said signal of the mixture at a time when less than in the step e) of said target binding agent present in said mixture has assumed the second position;
e) measuring said signal of the mixture for a second time at a time when more than in step d) of said target binding agent has assumed the second position if the sample contains said target polynucleotide; and
f) determining the relationship of the measurement results obtained in steps e) and d) and comparing it to a predetermined cut-off value that is characteristic for said mixture of sample and target binding agent to determine whether said target polynucleotide is present in the sample or not.

Preferred embodiments of these embodiments of the invention relate to a method comprising
a) providing a mixture of said sample and target binding agent and a second binding agent, said target binding agent being capable of assuming
 a first position where said target binding agent is not bound to said target polynucleotide or to said second binding agent and
 a second position where said target binding agent is bound to said target polynucleotide and
 a third position where said target binding agent is bound to said second binding agent, and a single target binding agent cannot simultaneously be in the second and third positions and a signal is measurable from said mixture, the intensity of said signal depending on the proportions of target binding agent being in said first, second and third positions;
b) exposing said mixture to a first condition where said target binding agent is in said first position;
c) exposing said mixture to a second condition where said target binding agent is capable of assuming the second and the third position, the proportion of target binding agent being in the second and third positions depending on the amount of target polynucleotide in said mixture;
d) measuring said signal of the mixture at a time when less than in step e) of said target binding agent present in said mixture has assumed the second or the third position;
e) measuring said signal of the mixture for a second time at a time when more than in step d) of said target binding agent has assumed the second or the third position; and
f) determining the relationship of the measurement results obtained in steps d) and e) and comparing it to a predetermined cut-off value that is characteristic for said mixture of sample and target binding agent to determine whether said target polynucleotide is present in the sample or not.

The present invention also relates to the use of a device comprising means for carrying out the methods of the invention according to the present invention. Said device would comprise means for regulating the temperature of a liquid mixture, and means for measuring and recording a signal from said liquid mixture. In a preferred embodiment, the device is capable of switching the condition to which a reaction mixture is exposed from the first condition to the second condition at a faster rate than the target binding agent present in said reaction mixture is capable of switching from the first position to the second and/or the third position.

The present invention also relates to the use of a kit comprising reagents for the method of the invention. The reagents comprise the target binding agent and optionally a second binding agent and preferably nucleic acid amplification reagents. Furthermore the kit may comprise the reaction vessel for the nucleic acid amplification reaction. The kit can also comprises the target binding agent and second binding agent and PCR reagents in dry form in the reaction vessel, such as described in WO2005118849. The reagents may contain any reagents described herein in context of the method of the present invention.

Next the invention is described by way of a non-limiting example relating to PCR reaction.

EXAMPLE 1

Detection of *Salmonella* sp. Using the Method of the Present Invention and Comparison of the Method of the Present Invention to a Real-Time Measurement Technique To demonstrate the functionality of the object of the present invention, a PCR assay for *Salmonella* sp. was set up. The assay was based on a dry chemistry principle described in WO2005118849. Detection was based on competitive hybridization, the principle of which is described e.g. in EP0232967B1. To briefly explain the detection principle, salmonella specific DNA is amplified by PCR in the assay from a sample in the presence of an oligonucleotide probe that is labelled with a stable and fluorescent terbium chelate. The terbium probe is designed so that it binds one strand of the amplified salmonella target polynucleotide and emits a high level of terbium fluorescence when free in solution (i.e. in its first position) or when bound to the target polynucleotide (i.e. in its second position). The terbium probe shall thus be understood as a "target binding agent" as the term is used herein. In addition to the terbium probe, a quencher probe was also used in the assay and shall be understood as a "second binding agent" as the term is used herein. The quencher probe was complementary to the terbium probe and labelled with Dabcyl, a dark quencher capable of quenching terbium fluorescence when brought into close proximity with the terbium label, i.e. when the terbium probe is in its third position, that is hybridized with the quencher probe. The terbium and quencher probe therefore form a pair that can be used to detect a target polynucleotide having a sequence that is complementary to the terbium and/or quencher probe sequence by means of competitive hybridization: in the presence of salmonella target DNA the reaction mixture emits a high level of terbium fluorescence because at least part of the terbium probe is bound to the salmonella DNA, while in the absence of salmonella DNA essentially all of the terbium probe is bound to the quencher probe and the reaction mixture thus only emits a very low level of fluorescence.

To demonstrate the functionality of the approach, a total of 18 food samples (à 25 g) were artificially inoculated with 1-10 CFU of salmonella, while 14 samples (à 25 g) were not inoculated. All samples were shaken in 225 ml of buffered peptone water at +37° C. for 6 hours, after which 10 millilitre samples were taken apart. *Salmonella* cells were purified from the 10 millilitre aliquots using the Magda *Salmonella* kit (Raisio Diagnostics). After capture of the bacterial cells, the magnetic particles were washed twice with physiological saline and suspended in 60 µl sterile water.

PCR reactions were performed on prototype dry chemistry *Salmonella* PCR reaction vessels manufactured by Abacus Diagnostica Ltd. Thermal cycling and time-resolved fluorescence measurements were performed using a prototype nucleic acid analyzer manufactured by Abacus Diagnostica Ltd. The thermal cycling principle has been described in WO2005118144. To start an assay, 30 µl of magnetic particles diluted in water were added into a reaction vessel after which the vessels were transferred into the nucleic acid analyzer. The analyzer comprises an array of thermal blocks maintained at predetermined temperatures. One of the blocks further accommodates a time-resolved fluorescence measurement unit that allows the measurement of time-resolved fluorescence emitted by the mixtures inside the reaction vessels. A PCR protocol consisting of 45 PCR cycles was run to generate enough salmonella specific PCR product. Real-time measurement data was collected by measuring, at 50° C., the time-resolved terbium fluorescence intensities emitted by the reactions after PCR cycle numbers 10 and 45.

After completion of the amplification reaction, measurement data was collected according to the present invention in the following manner: the reactions were heated to approximately 95° C. for 60 seconds to denature all nucleic acids in the reaction vessels, including the probes. After the denaturation step the reactions were transferred to the measurement block, the temperature of which was kept at 50° C. The reactions were incubated in the measurement block for 5 seconds, after which a first terbium fluorescence measurement was performed. After the measurement the reactions were incubated in the measurement block for 120 seconds during which period the terbium probe hybridized with the quencher probe and/or with the amplified salmonella DNA if salmonella DNA was amplified in the PCR reaction preceding the measurements. Then, after the 120 second incubation, a second terbium fluorescence measurement was performed. To analyze the results according to the present invention, the signal obtained in the second measurement (H) was divided by the signal obtained in the first measurement (D). A cut-off value of 0.35 had been pre-determined for the particular analytical dry chemistry PCR reaction vessels in the following manner: six replicate dry reagent vessels were reconstituted with sterile water and the average H/D (M) was determined for these six reactions. Furthermore, the standard deviation (SD) between the six replicate reactions was calculated. The cut-off value for all reaction vessels having the same concentrations of components was defined as M+2*SD, which equalled 0.35. To deduce the positivity/negativity of sample reactions, their determined H/D values were then compared to this pre-determined cut-off value. A result equal or above 0.35 was designated as positive and a result below 0.35 was designated as negative.

To compare the performance of the method of the present invention to the real-time measurement technique, the results were also analyzed using the real-time data collected at PCR cycles 10 and 45. The real-time data was analyzed by dividing the fluorescence signal obtained after PCR cycle 45 (S) by the signal recorded after PCR cycle 10 (N) to obtain a signal-to-noise ratio (S/N). If the signal-to-noise ratio was equal to or higher than 1.10, indicating that the signal had increased 10% during amplification, the sample was considered positive. A S/N value below 1.10 was considered negative.

The results are shown in table 1. As can be seen in the table, some of the samples analyzed using the real-time measurement data yielded a false negative result because the signal intensities in these reactions did not increase as a result of amplification. This may be caused by the fact that even if the target sequence was in fact amplified in PCR, the measured signal intensity did not increase because of, for example, appearance of bubbles in the reaction vessel. However, using the method of the present invention, the positivity/negativity of each reaction could be deduced correctly by comparing the obtained H/D value to the pre-determined cut-off value (0.35). It should be noted that the cut-off value was determined before the first samples were analyzed and the food samples were analyzed on six different days by four different operators using four individual analyzer instruments. Therefore, it can be concluded that the pre-determined cut-off allowed correct assignment of positivity/negativity despite differences in sample optical density, operator, instrument or day-to-day variations, which demonstrates that the object of the present invention allows homogeneous detection of a specific target polynucleotide to be done without the need to monitor nucleic acid amplification in real time and without the need to analyze negative or positive control reactions in parallel with actual samples and without the need to normalize measured fluorescence counts against the signal intensity of a second fluorescent indicator. In fact, these results demonstrate that the method of the present invention allows more accurate detection of nucleic acids than methods described in the prior art, e.g. real-time PCR.

Table 1. The results obtained for a total of 32 samples, 18 of which were spiked with 1-10 live salmonella cells. All of the spiked samples gave a positive result when analyzed using the method of the present invention (referred to as kinetic hybridization in the table), where fluorescence signals of hybridized probes are divided by the fluorescence signal of denatured probes and the qualitative result—positive or negative—is deduced by comparing the thus obtained H/D value to a pre-determined cut-off value, which in the case of this example was 0.35. However, when the same PCR reaction results were analyzed using the real-time data, false results were obtained for some samples. The false results are indicated by bold letters in the table. The false results are most probably due to unspecific effects on signal intensities. Thus, the method of the present invention allows more reliable analysis than the real-time measurement method.

| Sample matrix | Inoculation | H/D | Kinetic hybridization result | S/N | Real-time result |
|---|---|---|---|---|---|
| Pork meat | yes | 0.53 | Positive | 1.74 | Positive |
| Pork meat | yes | 0.62 | Positive | 2.09 | Positive |
| Pork meat | no | 0.24 | Negative | 0.85 | Negative |
| Pork meat | no | 0.24 | Negative | 1.08 | Negative |
| Beef meat | yes | 0.52 | Positive | 1.81 | Positive |
| Beef meat | yes | 0.5 | Positive | 1.52 | Positive |
| Beef meat | no | 0.22 | Negative | 0.71 | Negative |
| Beef meat | no | 0.27 | Negative | 0.73 | Negative |
| Pork meat | yes | 0.48 | Positive | 1.34 | Positive |
| Pork meat | yes | 0.37 | Positive | 0.96 | Negative |
| Pork meat | yes | 0.36 | Positive | 0.99 | Negative |
| Pork meat | yes | 0.55 | Positive | 1.41 | Positive |
| Pork meat | yes | 0.69 | Positive | 2.06 | Positive |
| Pork meat | no | 0.25 | Negative | 0.89 | Negative |
| Pork meat | no | 0.25 | Negative | 0.87 | Negative |
| Pork meat | no | 0.25 | Negative | 0.93 | Negative |
| Sliced chicken | yes | 0.69 | Positive | 1.25 | Positive |
| Sliced chicken | yes | 0.6 | Positive | 0.95 | Negative |
| Sliced chicken | yes | 0.67 | Positive | 1.24 | Positive |
| Sliced chicken | yes | 0.57 | Positive | 1.27 | Positive |
| Sliced chicken | yes | 0.7 | Positive | 2.10 | Positive |
| Sliced chicken | no | 0.25 | Negative | 0.84 | Negative |
| Sliced chicken | no | 0.26 | Negative | 0.90 | Negative |
| Sliced chicken | no | 0.29 | Negative | 0.88 | Negative |
| Egg | yes | 0.56 | Positive | 1.63 | Positive |
| Egg | yes | 0.63 | Positive | 2.26 | Positive |
| Egg | yes | 0.66 | Positive | 2.59 | Positive |
| Egg | no | 0.25 | Negative | 0.81 | Negative |
| Egg | no | 0.23 | Negative | 0.85 | Negative |
| Egg | no | 0.29 | Negative | 1.03 | Negative |
| Milk | yes | 0.4 | Positive | 1.03 | Negative |
| Milk | no | 0.26 | Negative | 0.90 | Negative |

EXAMPLE 2

Detection of a Polynucleotide Using the Method of the Present Invention and a Prompt Fluorophore Label To demonstrate that the method of the present invention can be performed using not only lanthanide labels but other labels as well, a homogeneous PCR assay based on competitive hybridization for a salmonella internal amplification control was set up. The target sequence (IAC) was constructed as described by Perelle, S., Dilasser, F., Malorny, B., Grout, J., Hoorfar, J. and Fach, P. in "Comparison of PCR-ELISA and LightCycler real-time PCR assays for detecting Salmonella spp. in milk and meat samples", published in Molecular and Cellular Probes, vol. 18, pp. 409-420, 2004. PCR and the method of the present invention was performed as described in Example 1 above except that instead of a terbium labelled probe and its complementary quencher probe, an oligonucleotide probe specific for the IAC and labelled at its 5'-end with 6-carboxyfluorescein (FAM) was used for detection and FAM signals were recorded instead of terbium signals in the measurements. Two kinds of reactions were performed: negative reactions without any target nucleic acid (n=4) and positive reactions that contained IAC diluted in water (n=4). The H/D values were determined for the individual reactions as described in example 1 above. For the individual negative reactions, the H/D values were 0.504, 0.495, 0.502 and 0.498. For the positive reactions, the corresponding H/D values were, as expected, significantly greater, namely 0.953, 0.952, 0.942 and 0.944. In conclusion, the method of the present invention functions perfectly using different kinds of labels for detection.

The invention claimed is:

1. A method for detection of the presence of a target polynucleotide in a sample, said method comprising
   a) providing a mixture of said sample, nucleic acid amplification reagents and a target binding agent, said target binding agent being capable of assuming a first position where said target binding agent is not bound to said target polynucleotide and a second position where said target binding agent is bound to said target polynucleotide, and a signal is measurable from said mixture, the intensity of said signal depending on the proportions of target binding agent being in said first and second positions;
   b) exposing said mixture to conditions that allow nucleic acid amplification to occur in said mixture and allowing said amplification to complete;
   c) exposing said mixture to a first condition resulting in that said target binding agent is in said first position;
   d) exposing said mixture to a second condition where said target binding agent is capable of assuming the second position;
   e) measuring at least once, after completion of said nucleic acid amplification and after said mixture has been exposed to said first condition, said signal of the mixture at a first time when less than in the step f) of said target binding agent present in said mixture has assumed the second position;
   f) measuring at least once, after completion of said nucleic acid amplification and after said mixture has been exposed to said second condition, said signal of the mixture at a second time when, if the sample contains said target polynucleotide, more than in step e) of said target binding agent has assumed the second position; and g) determining the ratio of the measurement results obtained in steps e) and f) and comparing it to a predetermined cut-off value that is characteristic for said mixture of sample and target binding agent to determine whether said target polynucleotide is present in the sample.

2. The method according to claim 1, wherein step f) is carried out after exposing the mixture to a second condition for a time sufficient for at least 30% of the target binding agent to reach second position.

3. The method according to claim 1, wherein the mixture further comprises a second binding agent and the target binding agent is capable of assuming a third position where said target binding agent is bound to said second binding agent, and a single target binding agent cannot simultaneously be in the second and third positions and a signal is measurable from said mixture, the intensity of said signal depending on the proportions of target binding agent being in said first, second and third positions and in step f) the signal is measured at least once when after said mixture has been exposed to said second condition at a time when more than in step e) of said target binding agent has assumed the second or the third position.

4. The method according to claim 1, wherein more than one target polynucleotide, each of them having their own specific target binding agent, are detected in the same reaction.

5. The method according to claim 1, wherein more than one kind of target binding agent is used to detect one kind of target polynucleotide.

6. The method according to claim 1, wherein the signal is an optical signal.

7. The method according to claim 1, wherein the temperature of the first condition is at least 10° C. higher than that of the second condition.

8. The method according to claim 7, wherein the temperature of the first condition is at least 10° C. higher than that of the second condition.

9. The method according to claim 1, wherein the first and the second conditions are achieved chemically.

10. The method according to claim 1, wherein the mixture is exposed to conditions that allow nucleic acid amplification to occur in said mixture and the measuring of steps e) and/or f) is carried out at least once during said amplification.

11. The method according to claim 1, wherein the target polynucleotide is a PCR product.

12. The method according to claim 1, wherein the target binding agent is selected from nucleic acids, nucleic acid analogs, nucleic acid binding chemicals, intercalating dyes, proteins and metal ions.

13. The method according to claim 3, wherein the second binding agent is selected from nucleic acids, nucleic acid analogs, nucleic acid binding chemicals, intercalating dyes, proteins and metal ions.

14. The method according to claim 13, wherein the target binding agent and/or second binding agent is an oligonucleotide labeled with a label selected from the group consisting of enzymes, enzyme substrates, radioactive atoms, fluorophores, light absorbing groups, chromophores, chemiluminescent labels, electrochemiluminescent labels and ligands having specific binding partners.

15. The method according to claim 14, wherein said light absorbing groups are dark quenchers.

16. The method according to claim 14, wherein the oligonucleotide is labeled with a fluorophore selected from prompt fluorophores, labels with long emission lifetimes, and luminescent particles.

17. The method according to claim 16, wherein said prompt fluorophores are selected from the group consisting of 6-carboxyfluorescein (FAM), tetramethylrhodamine, TAMRA, HEX, TET, JOE, VIC, EDANS, ROX, green fluorescent protein, fluorescent nucleotides and nucleotide derivatives and analogs.

18. The method according to claim 16, wherein said labels with long emission lifetimes are selected from the group consisting of lanthanide chelates and lanthanide cryptates.

19. The method according to claim 1, wherein the target binding agent is an oligonucleotide labeled with at least two different kinds of labels, and said labels are capable of interacting with each other when brought to close proximity with each other.

20. The method according to claim 3, wherein a first label is incorporated in the target binding agent and a second label is incorporated in the second binding agent and said first and second labels are capable of interacting with each other when the target binding agent is in said third position.

21. The method according to claim 1, wherein said signal is measured by time-resolved fluorometry.

* * * * *